ting et al.

(12) United States Patent
Jain et al.

(10) Patent No.: US 10,204,416 B2
(45) Date of Patent: Feb. 12, 2019

(54) AUTOMATIC DESKEW USING DESIGN FILES OR INSPECTION IMAGES

(71) Applicant: KLA-Tencor Corporation, Milpitas, CA (US)

(72) Inventors: Arpit Jain, Indore (IN); Arpit Yati, Lucknow (IN); Thirupurasundari Jayaraman, Chennai (IN); Raghavan Konuru, Kurnnol (IN); Raj Kuppa, Santa Clara, CA (US); Hema Prasad, Chennai (IN); Saiyashwanth Momula, Telangana (IN); Arun Lobo, Karnataka (IN)

(73) Assignee: KLA-Tencor Corporation, Milpitas, CA (US)

( * ) Notice: Subject to any disclaimer, the term of this patent is extended or adjusted under 35 U.S.C. 154(b) by 40 days.

(21) Appl. No.: 15/258,546

(22) Filed: Sep. 7, 2016

(65) Prior Publication Data

US 2017/0228866 A1 Aug. 10, 2017

Related U.S. Application Data

(60) Provisional application No. 62/309,623, filed on Mar. 17, 2016.

(30) Foreign Application Priority Data

Feb. 4, 2016 (IN) .............................. 201641004030

(51) Int. Cl.
*H04N 7/18* (2006.01)
*G06T 7/00* (2017.01)
(Continued)

(52) U.S. Cl.
CPC ....... *G06T 7/0044* (2013.01); *G01N 23/2251* (2013.01); *G06T 7/001* (2013.01);
(Continued)

(58) Field of Classification Search
CPC ........ G06F 17/00; G01N 21/00; G01N 23/00; G06T 7/00; H04N 7/00; H01L 21/00
See application file for complete search history.

(56) References Cited

U.S. PATENT DOCUMENTS 5,479,252 A 12/1995 Worster et al.
5,847,821 A 12/1998 Tracy et al.
(Continued)

FOREIGN PATENT DOCUMENTS

JP 2011205019 A 10/2011

OTHER PUBLICATIONS

ISA/KR, International Search Report for PCT/US2017/015880 dated May 12, 2017.

*Primary Examiner* — Maryam A Nasri
(74) *Attorney, Agent, or Firm* — Hodgson Russ LLP

(57) ABSTRACT

Deskew for image review, such as SEM review, aligns inspection and review coordinate systems. Deskew can be automated using design files or inspection images. A controller that communicates with a review tool can align a file of the wafer, such as a design file or an inspection image, to an image of the wafer from the review tool; compare alignment sites of the file to alignment sites of the image from the review tool; and generate a deskew transform of coordinates of the alignment sites of the file and coordinates of alignment sites of the image from the review tool. The image of the wafer may not contain defects.

20 Claims, 7 Drawing Sheets

(51) Int. Cl.
*H01J 37/22* (2006.01)
*G01N 23/2251* (2018.01)
*H01L 21/66* (2006.01)

(52) U.S. Cl.
CPC ............ *H01J 37/222* (2013.01); *H01L 22/20* (2013.01); *G06T 2207/10061* (2013.01); *G06T 2207/30148* (2013.01)

(56) References Cited

U.S. PATENT DOCUMENTS

| | | | |
|---|---|---|---|
| 6,410,927 | B1 | 6/2002 | Pike |
| 6,898,742 | B2 | 5/2005 | Koyanagi et al. |
| 6,996,738 | B2 | 2/2006 | Chiang |
| 7,167,995 | B2 | 1/2007 | Chiang |
| 7,433,509 | B1 * | 10/2008 | Zhou .................... G06K 9/3275 382/144 |
| 8,045,790 | B2 | 10/2011 | Zhou et al. |
| 2002/0199141 | A1 | 12/2002 | Lemlein et al. |
| 2005/0094136 | A1 * | 5/2005 | Xu ........................ G01N 21/21 356/237.3 |
| 2005/0122508 | A1 * | 6/2005 | Uto ....................... G01N 21/956 356/237.2 |
| 2007/0222991 | A1 * | 9/2007 | Spady ...................... G02B 7/00 356/401 |
| 2008/0032429 | A1 * | 2/2008 | Chen .................. G01N 21/8851 438/14 |
| 2008/0144055 | A1 * | 6/2008 | Sussmeier ........... G06F 17/2211 358/1.9 |
| 2010/0329576 | A1 * | 12/2010 | Tian ......................... G06K 9/00 382/218 |
| 2011/0305393 | A1 * | 12/2011 | Nijemcevic .......... G06K 9/3283 382/182 |
| 2012/0131529 | A1 * | 5/2012 | Hayakawa ......... G01N 21/8851 716/112 |
| 2012/0314054 | A1 | 12/2012 | Chou et al. |
| 2013/0114881 | A1 | 5/2013 | Harada et al. |
| 2014/0353498 | A1 | 12/2014 | Shur |
| 2015/0125065 | A1 | 5/2015 | Lee et al. |
| 2017/0047195 | A1 * | 2/2017 | Lee ....................... H01J 37/222 |

* cited by examiner

AUTOMATIC DESKEW USING DESIGN FILES OR INSPECTION IMAGES

CROSS-REFERENCE TO RELATED APPLICATIONS

This application claims priority to Indian Application No. 201641004030 filed Feb. 4, 2016 and U.S. Application Ser. No. 62/309,623 filed Mar. 17, 2016, the disclosures of which are hereby incorporated by reference.

FIELD OF THE DISCLOSURE

This disclosure relates to semiconductor wafer review and analysis.

BACKGROUND OF THE DISCLOSURE

Wafer inspection systems help a semiconductor manufacturer increase and maintain integrated circuit (IC) chip yields by detecting defects that occur during the manufacturing process.

One purpose of inspection systems is to monitor whether a manufacturing process meets specifications. The inspection system indicates the problem and/or the source of the problem if the manufacturing process is outside the scope of established norms, which the semiconductor manufacturer can then address.

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

Semiconductor manufacturers needs to review images or results from an area of a wafer or semiconductor device, such as areas flagged during inspection. This is challenging because the images or results may not easily align to an inspection image or to a design file. This also is challenging because the various images, results, or design files may use different coordinate systems. For example, a user of a scanning electron microscope (SEM) review tool may need to align an image from the SEM with an inspection image. This can be accomplished through manual deskew, offset correction, or automatic deskew, but these techniques each have drawbacks.

For manual deskew, the locations given by the inspection tool are viewed on a review tool, such as an SEM, and an actual location of defects is marked. Only real defects can be used for this technique. Manual deskew will not work in a semiconductor manufacturing setting with defect-free devices or defect-free parts of a wafer. The offsets between the command location and actual defect location are calculated. The calculated offsets are translational, rotational, scaling, and non-orthogonality between the review and inspection coordinate systems. A deskew transform is generated, which is then applied to all defect locations of given defect coordinates of a particular scan. The generated deskew transform can be stored in a cache which can be used for further recipe job runs.

Manual deskew has multiple drawbacks. Manual deskew is a tedious and time-consuming technique because a user needs to search for real defects across the entire wafer. These defects may need to be greater than a particular size threshold to be viewable. Performing the deskew pass and the time taken for deskew depends on a user's knowledge and experience. Manual deskew requires presence of real defects with a particular size all across the wafer. If the defects are too small, it is difficult to find in the higher field of view (FOV), which may be required for accommodating the deskew errors. Very large defects cannot be used because a user does not know which part of the large defect is flagged by the inspection system. Furthermore, on high SEM non-visible (SNV) rate inspections, real defects are very difficult to find and manual deskew is impractical.

For offset correction, a number of real defects are manually marked and translational offset between the command location and actual defect location is calculated by the software. Offset correction will not work in a semiconductor manufacturing setting with defect-free devices or defect-free parts of a wafer. The calculated translational offsets are used to calculate the mean translational offset between the review and inspection coordinate systems. Offset correction can only correct for translational offsets between the two coordinate systems. Offset correction suffers from all the other disadvantages of manual deskew. Furthermore, offset correction only corrects for translational offset. Other errors between the review and inspection coordinate systems are ignored.

Automatic deskew does not manually mark the defects. Instead, the defect locations are automatically detected using a defect detection algorithm. Similar to manual deskew, translational, rotational, scaling, and non-orthogonality offsets are calculated. However, this deskew solution is not robust and frequently fails. For example, automatic deskew can fail if a capture rate on the layer is insufficient. In another example, one or more reference images are needed with the defect site image, which increases complexity and can increase failure rates. Automatic deskew has seen limited commercial use due to reliability issues. Like manual deskew, automatic deskew requires presence of defects of a particular size across the wafer. Automatic deskew will not work in a semiconductor manufacturing setting with defect-free devices or defect-free parts of a wafer. Furthermore, this deskew technique is impractical on high SNV rate inspections.

Therefore, improved deskew techniques are needed.

BRIEF SUMMARY OF THE DISCLOSURE

In a first embodiment, a system is provided. A system comprises a review tool; an electronic data storage unit in which one or more reference files are stored; and a controller in electronic communication with the review tool. The review tool includes a stage configured to hold a wafer and an image generation system configured to generate an image of the wafer. The controller is configured to receive the image of the wafer from the review tool; identify one or more alignment sites in the image of the wafer; receive a reference file corresponding to the image of the wafer from the review tool from the electronic data storage unit; mark at least one die corner on the wafer; compare one or more alignment sites in the reference file to one or more alignment sites in the image from the review tool; and generate a deskew transform corresponding to the image of the wafer based on the one or more alignment sites. Each reference file has one or more alignment sites. The controller can include a processor and a communication port in electronic communication with the processor and the electronic data storage unit. The review tool can be a scanning electron microscope. The reference file can be, for example, a design file or an inspection image of the wafer. The image of the wafer may not contain a defect having a size from 3 μm to 50 μm.

The image generation system can be configured to use at least one of an electron beam, a broad band plasma, or a laser to generate the image of the wafer.

The controller can further be configured to apply the deskew transform to the image of the wafer. The controller also can further be configured to validate that the image of the wafer from the review tool and the design file remain aligned after the deskew transform is applied.

In a second embodiment, a method is provided. The method comprises loading a wafer on a stage of a review tool; receiving, from the review tool, an image of the wafer having one or more alignment sites; receiving, at a controller, a design file corresponding to the wafer; marking at least one die corner on the wafer; comparing, using the controller, the one or more alignment sites of the design file to the one or more alignment sites of the image from the review tool; and generating, using the controller, a deskew transform corresponding to the image of the wafer based on the one or more alignment sites. The design file has one or more alignment sites. The image of the wafer from the review tool can be a scanning electron microscope image. The image of the wafer may not contain a defect having a size from 3 μm to 50 μm.

The method can further comprise applying the deskew transform to the image using the controller. The method can further comprise validating, using the controller, that the image of the wafer from the review tool and the design file remain aligned after applying the deskew transform.

In a third embodiment, a method is provided. The method comprises loading a wafer on a stage of a review tool; receiving, from the review tool, an image of the wafer; receiving, at a controller, an inspection image corresponding to the wafer; marking at least one die corner on the wafer; comparing, using the controller, alignment sites of the inspection image to alignment sites of the image from the review tool; and generating, using the controller, a deskew transform corresponding to the image of the wafer based on the one or more alignment sites. The image of the wafer from the review tool can be a scanning electron microscope image. The image of the wafer may not contain a defect having a size from 3 μm to 50 μm.

The method can further comprise applying the deskew transform to the image of the wafer using the controller. The method also can further comprise validating, using the controller, that the image of the wafer from the review tool and the inspection image remain aligned after applying the deskew transform. The method also can further comprise manually marking at least one deskew site on the image of the wafer from the review tool and calculating an offset between the inspection image and the image from the review tool based on the marked deskew site.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments disclosed herein perform deskew for image review, such as SEM review. Deskew aligns inspection and review coordinate systems to reduce the defect location accuracy (DLA) seen during review on an SEM tool. Deskew can be automated using reference files, such as design files or inspection images.

Embodiments of the deskew techniques disclosed herein avoid the drawbacks of previous techniques. First, offsets can be calculated by aligning an image of a wafer and an inspection image or design file. This can reduce use of defect detection algorithms, which have led to failure with automatic deskew. Only a single image of a wafer may be needed, which reduces complexity and improves reliability. Defects are not required for these techniques to function, which increases applicability. Whereas automatic deskew relies on real defects, these techniques can use unique sites, which need not always be a defect. Unique sites can be found more readily across a wafer.

Figure 1:
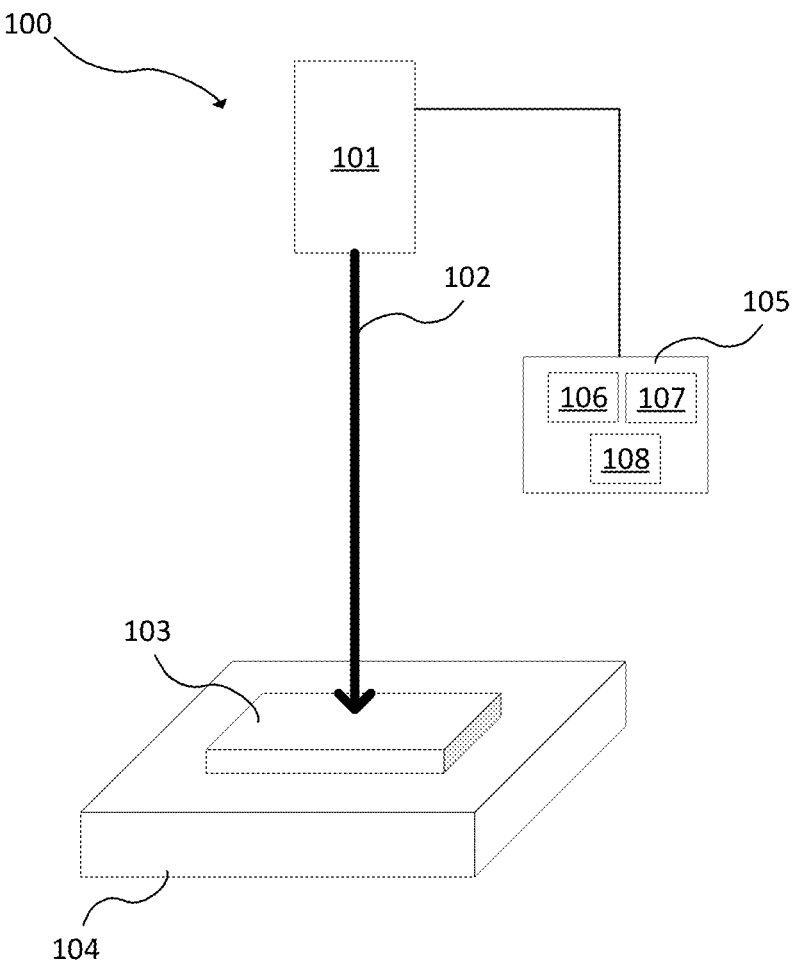
FIG. 1 is a block diagram of a defect review tool in accordance with the present disclosure.

FIG. 1 is a block diagram of a defect review tool 100 in accordance with the present disclosure. The defect review tool 100 includes a stage 104 configured to hold a wafer 103 or other workpieces. The stage 104 may be configured to move or rotate in one, two, or three axes.

The defect review tool 100 also includes an image generation system 101 configured to generate an image of a surface of the wafer 103. The image may be for a particular layer of the wafer 103. In this example, the image generation system 101 produces an electron beam 102 to generate an image of the wafer 103. Other image generation systems 101 are possible, such as those that use broad band plasma or laser scanning.

As used herein, the term "wafer" generally refers to substrates formed of a semiconductor or non-semiconductor material. Examples of such a semiconductor or non-semiconductor material include, but are not limited to, monocrystalline silicon, gallium nitride, gallium arsenide, indium phosphide, sapphire, and glass. Such substrates may be commonly found and/or processed in semiconductor fabrication facilities.

A wafer may include one or more layers formed upon a substrate. For example, such layers may include, but are not limited to, a photoresist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features or periodic structures. Formation and processing of such layers of material may ultimately result in completed devices. Many different types of devices may be formed on a wafer, and the term wafer as used herein is intended to encompass a wafer on which any type of device known in the art is being fabricated.

In a particular example, the defect review tool 100 is part of or is a scanning electron microscope (SEM). Images of the wafer 103 are generated by scanning the wafer 103 with a focused electron beam 102. The electrons are used to produce signals that contain information about the surface topography and composition of the wafer 103. The electron beam 102 can be scanned in a raster scan pattern, and the position of the electron beam 102 can be combined with the detected signal to produce an image.

The defect review tool 100 communicates with a controller 105. For example, the controller 105 can communicate with the image generation system 101 or other components of the defect review tool 100. The controller 105 can include a processor 106, an electronic data storage unit 107 in electronic communication with the processor 106, and a communication port 108 in electronic communication with the processor 106. It is to be appreciated that the controller 105 may be implemented in practice by any combination of hardware, software, and firmware. Also, its functions as described herein may be performed by one unit, or divided up among different components, each of which may be implemented in turn by any combination of hardware, software and firmware. Program code or instructions for the controller 105 to implement the various methods and functions described herein may be stored in controller readable storage media, such as a memory in the electronic data storage unit 107, within the controller 105, external to the controller 105, or combinations thereof.

The controller 105 may be coupled to the components of the defect review tool 100 in any suitable manner (e.g., via one or more transmission media, which may include "wired" and/or "wireless" transmission media) such that the controller 105 can receive the output generated by the defect review tool 100, such as output from the imaging device 101. The controller 105 may be configured to perform a number of functions using the output. For instance, the controller 105 may be configured to review defects on the wafer 103 using the output. In another example, the controller 105 may be configured to send the output to an electronic data storage unit 107 or another storage medium without performing defect review on the output. The controller 105 may be further configured as described herein.

The controller 105, other system(s), or other subsystem(s) described herein may take various forms, including a personal computer system, image computer, mainframe computer system, workstation, network appliance, internet appliance, or other device. In general, the term "controller" may be broadly defined to encompass any device having one or more processors that executes instructions from a memory medium. The subsystem(s) or system(s) may also include any suitable processor known in the art such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

An additional embodiment relates to a non-transitory computer-readable medium storing program instructions executable on a controller for performing a computer-implemented method for identifying abnormalities on a wafer or detecting compliance/non-compliance, as disclosed herein. In particular, as shown in FIG. 1, electronic data storage unit 107 or other storage medium may contain non-transitory computer-readable medium that includes program instructions executable on the controller 105. The computer-implemented method may include any step(s) of any method(s) described herein.

Program instructions implementing methods such as those described herein may be stored on computer-readable medium, such as in the electronic data storage unit 107 or other storage medium. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Controller 105 may be configured according to any of the embodiments described herein. For example, the controller 105 may be programmed to perform some or all of the steps of FIG. 10 or FIG. 11. In an instance, the controller is configured to receive an image of the wafer from the review tool; identify one or more alignment sites in the image; receive a reference file from an electronic data storage unit corresponding to the image of the wafer from the review tool; align the reference file of the wafer to the image of the wafer from the review tool (e.g., marking at least one die corner on the wafer); compare one or more alignment sites in the reference file to one or more alignment sites in the image from the review tool; and generate a deskew transform corresponding to the image of the wafer based on the one or more alignment sites. The electronic data storage unit may contain one or more reference files, such as design files or inspection images.

While disclosed as part of a process control system, the controller 105 described herein may be configured for use with inspection systems. In another embodiment, the controller 105 described herein may be configured for use with a metrology system. Thus, the embodiments of as disclosed herein describe some configurations for classification that can be tailored in a number of manners for systems having different imaging capabilities that are more or less suitable for different applications.

Figure 8:
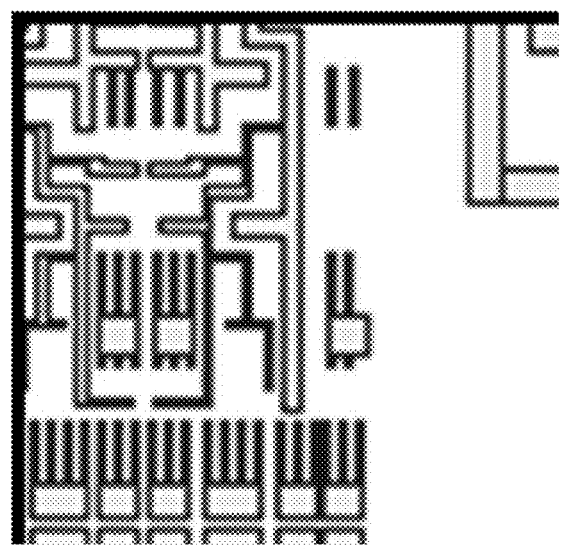
FIG. 8 shows an exemplary alignment site in a design clip.
Figure 9:
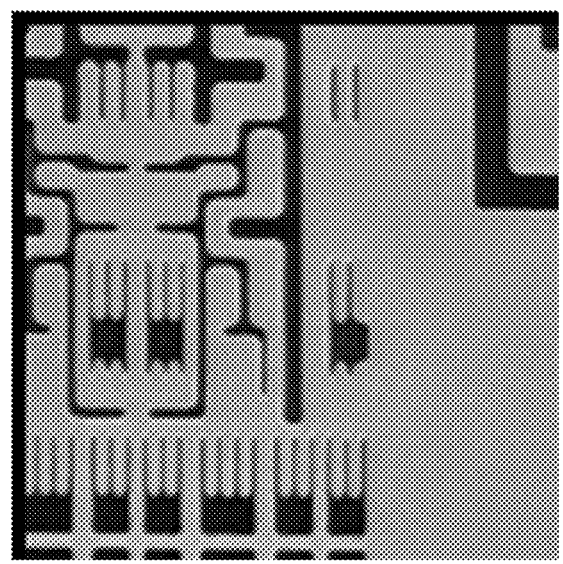
FIG. 9 shows an exemplary SEM image of the alignment site of FIG. 8.
Figure 10:
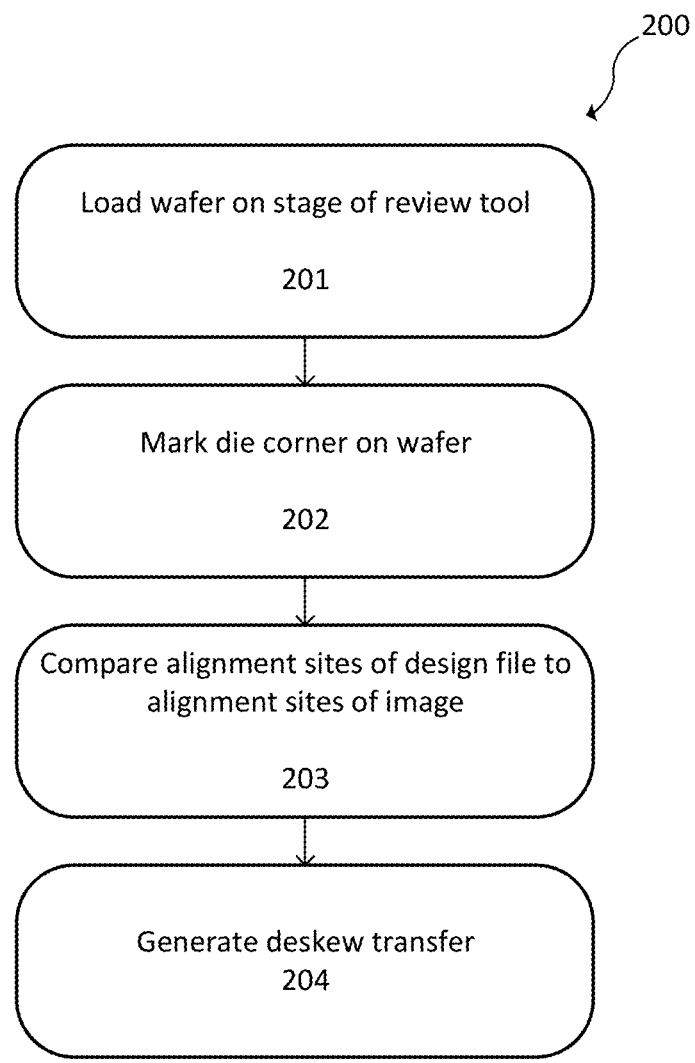
FIG. 10 is a flowchart of a first embodiment in accordance with the present disclosure.

FIG. 10 is a flowchart of a first embodiment for generating a deskew transform using design clips. Design clips are parts of a design file that contains the physical layout of a device. For example, see FIGS. 8 and 9 for an exemplary design clip and a corresponding SEM image.

For inspection scans on advanced inspection tools, a design file or physical layout file is closely aligned with the wafer using specially identified alignment targets or reference structures across the pattern. These alignment sites or reference structures may be either manually marked or automatically identified. There may be one or more alignment sites or reference structures per wafer or per die. For such inspections the wafer and design are closely aligned with each other. Therefore, design clips for locations in an inspection coordinate system can be extracted with high accuracy.

In the method 200, a wafer is loaded 201 on a stage of a review tool. The review tool may be, for example, the defect review tool 100. In an instance, the review tool may be an SEM. An image from the review tool of the wafer having one or more alignment sites can be received. The controller can receive a design file corresponding to the wafer having one or more alignment sites.

A design file is aligned 202 to an image from the review tool by marking a die corner. For example, an inspection tool can align the design file with an inspection coordinate system. Marking at least one die corner can provide coarse initial alignment between the image and the design file. Design clips at an inspection coordinate location of a unique site can be captured using this technique. The die corner can be marked either manually by a user or automatically using the die corner images or any other unique site images from the inspection tool as a reference.

An additional coarse alignment step also may be performed after the die corners are marked. For example, the design file and the image may be aligned using an image alignment algorithm or manually by a user.

Alignment sites of the design file are compared 203 to alignment sites of the image. The design file and the image may use the same coordinate system. The alignment sites in the design file can be correlated with the image of alignment site either automatically (e.g., using an image alignment algorithm or another technique) or manually where a user marks the common point between the design file and the image.

A deskew transform of coordinates of the alignment sites of the design file and coordinates of alignment sites of the image from the review tool is generated 204. Deskew offsets can be calculated by correlating design clips with unique alignment sites or other reference structures across the wafer with an image grabbed in the review tool at inspection coordinates for those unique sites. The deskew transform can be generated without relying upon real defects. Thus, defect-free devices or features can be used for deskew. In an example, the image of the wafer may not contain any defects having a size from 3 μm to 50 μm. These defects may be visible defects or other defects capable of being found using, for example, a defect review tool such as an SEM.

Figure 12:
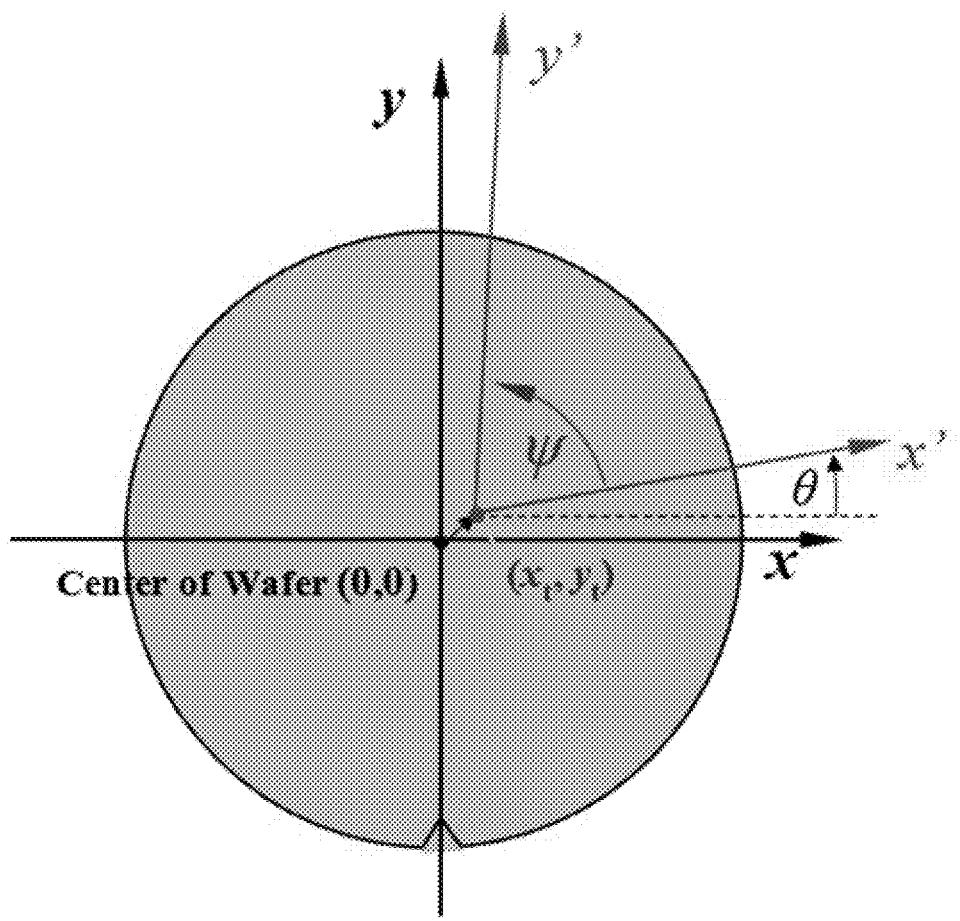
FIG. 12 illustrates an exemplary deskew transform.

The deskew transform may be the wafer-level conversion transform between the review and inspection coordinate systems, which incorporates correction for translational, rotational, scaling, and/or non-orthogonality offsets between the review and inspection coordinate systems. FIG. 12 illustrates an exemplary deskew transform. The $m_x$ and $m_y$ address scaling, functions of $\theta$ address rotation, functions of $\psi$ address non-orthogonality, and $x_t$ and $y_t$ address translation.

The unique sites can be manually selected, can be chosen based on which areas were inspected, and/or can be selected using an algorithm. Unique sites can be a device component. In an example, the unique sites can be a scribe line or streets crossing between dies and reticles. In another example, the unique sites can be a static random-access memory (SRAM) cell corner. The unique sites can have sizes from 3 μm to 50 μm, including all values and ranges to the 1 μm therebetween, though other sizes or dimensions are possible.

For calculation of deskew offsets, one or more unique alignment sites or reference structures may be used. These alignment sites or reference structures may be same or different than those used for alignment between a wafer and a design on an inspection tool.

Deskew offset calculation can be performed using automatic or manual correlation of design clips and review images.

The deskew transform can be applied to the image, such as using a controller. The controller can then validate that the image of the wafer from the review tool and the design file are or remain aligned.

The deskew transform of FIG. 10 can be performed automatically.

Figure 2:
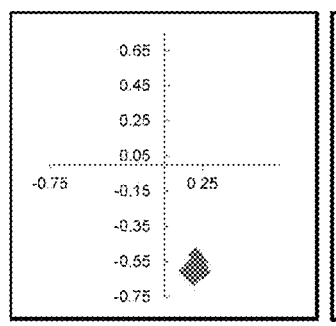
FIG. 2 is an example without deskew showing an offset.
Figure 3:
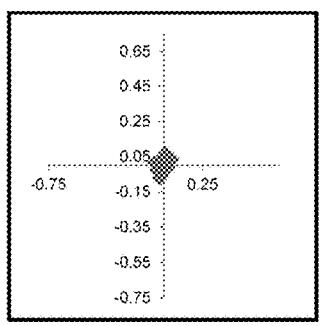
FIG. 3 is the example of FIG. 2 with manual deskew at defect locations.
Figure 4:
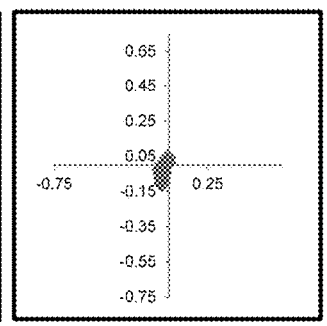
FIG. 4 is the example of FIG. 2 with automatic deskew at alignment sites using an embodiment in accordance with the present disclosure.

A proof of concept experiment was done by calculating deskew offsets using single and multiple alignment sites used on an inspection tool for wafer-to-design alignment. These alignment sites were automatically identified by algorithms on the inspection tool as unique sites to be used for alignment. An inspection recipe was set up on the inspection tool and a scan was taken. An algorithm automatically found unique alignment sites and automatically aligned wafer-to-design using these alignment sites during the scan. Design clips at the unique alignment sites used during inspection were extracted. Unique alignment sites were added as additional defects to the inspection result. The inspection result and wafer were loaded into an SEM tool. Reviews were run for three different cases, as illustrated in FIGS. 2-4. These cases were no deskew (FIG. 2), manual deskew (FIG. 3), and automatic deskew (FIG. 4). No deskew (FIG. 2) shows an offset. The automatic deskew used the method illustrated in FIG. 10 to correlate design clips at alignment sites with corresponding SEM images. Scatter plots for defects were generated and results were compared.

FIG. 2 is scatter plot for job run without any deskew step. Since no deskew correction is done here, an offset on defect positions is seen in the scatter plot. FIG. 3 is scatter plot for a job run with manual deskew. During manual deskew, the offsets between the inspection and review coordinate systems are corrected by a user marking the real defects manually. This is the conventional method. FIG. 4 is scatter plot for job run using deskew transform generated by offsets calculated automatically by aligning a unique site SEM image and a design file as disclosed in FIG. 10. This scatter plot is similar to that of manual deskew. Thus, the technique disclosed herein is validated as being as effective as manual deskew, but is faster. Unlike manual deskew, the technique disclosed herein does not require the presence of defects.

Figures 5, 6, 7:
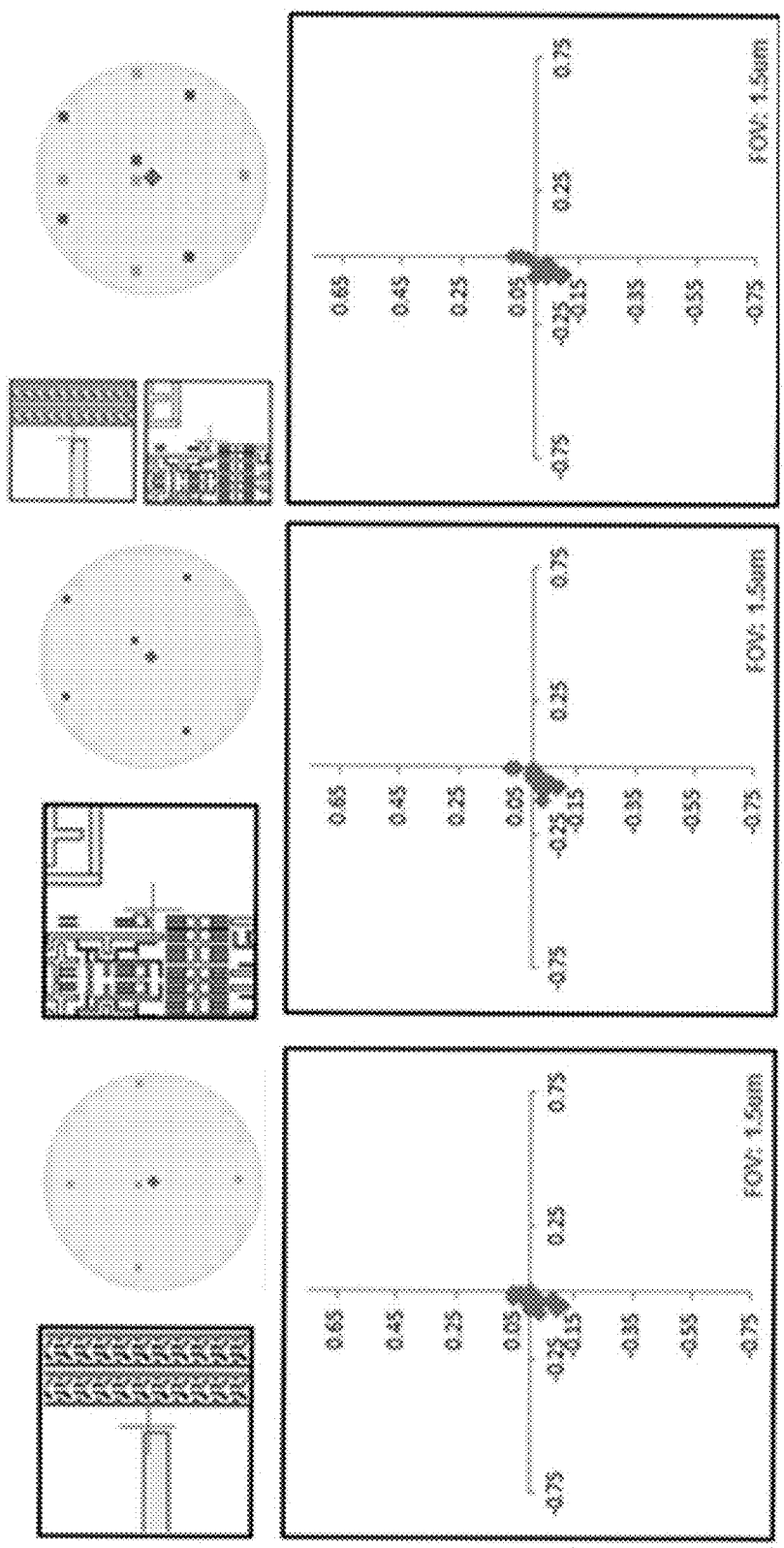
FIG. 5 shows exemplary results using a first alignment site.
FIG. 6 shows exemplary results using a second alignment site.
FIG. 7 shows exemplary results using the first and second alignment sites of FIGS. 5 and 6.

To check the repeatability, the experiment was repeated for another alignment site and using both alignment sites together. The offset with no deskew was removed in all the cases. The results are shown FIGS. 5-7. Use of multiple alignment sites may improve results, but a single alignment site may be sufficient for a deskew transform.

Figure 11:
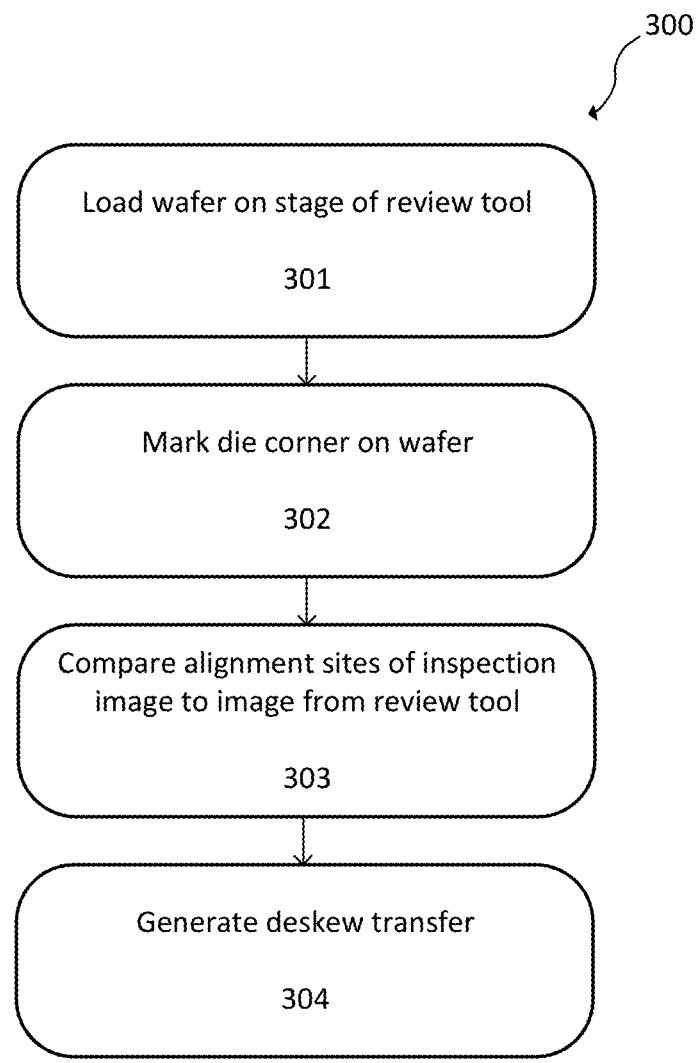
FIG. 11 is a flowchart of a second embodiment in accordance with the present disclosure.

FIG. 11 is a flowchart of a second embodiment for generating deskew using review image to optical image alignment. Deskew offsets can be calculated by aligning an inspection image grabbed on an inspection tool with an image grabbed at the same location across the wafer on the review tool. The sites chosen for this methodology can be one or more unique alignment sites or reference structure as selected in the embodiment of FIG. 10.

For the embodiment of FIG. 11, one or more alignment sites, at least one die corner location, and at least one optical image for locations chosen for the deskew offset calculation are provided. For example, the alignment sites, die corner location, and optical image are generated or provided by the inspection tool.

In the method 300, a wafer is loaded 301 on a stage of a review tool. The review tool may be, for example, the defect review tool 100. In an instance, the review tool may be an SEM. An image of the wafer from the review tool can be received. A controller can receive an inspection image corresponding to the wafer.

At least one die corner on the wafer is marked 302. In an example, die corners are automatically marked. Marked die corners enable the coordinate systems of the review tool and the inspection tool to be aligned. For example, the die corner can be marked on the inspection tool first. The same die corner then can be marked on the review tool. The die corner can be manually marked or can be automatically marked using die corner images or other unique site images from the inspection tool as a reference.

Initial alignment of an inspection image to a review image may either be done to mark at least one die corner initially, such as in step 302, or may be used for calculation of offsets between inspection and review images in a deskew transform calculation. For example, inspection alignment sites can be used for pattern match.

As with the embodiment of FIG. 10, additional coarse alignment techniques besides marking a die corner can be performed.

Alignment sites of the inspection image are compared 303 to alignment sites of the image from the review tool. The images may use the same coordinate system. The inspection image and the review image at the alignment sites can be compared either automatically using a pattern match algorithm or manually by a user. The output from this comparison will be the offset between the inspection and review images across the wafer, which can be used for a deskew transform calculation.

A deskew transform of coordinates of the alignment sites of the inspection image and coordinates of alignment sites of the image from the review tool is generated 304. Deskew offsets can be calculated by correlating the inspection image with unique alignment sites or other reference structures across the wafer with an image grabbed in the review tool at inspection coordinates for those unique sites. For example, see FIG. 12. The deskew transform can be generated without relying upon real defects. Thus, defect-free devices or features can be used for deskew. In an example, the image of the wafer may not contain a defect having a size from 3 μm to 50 μm. These defects may be visible defects or other defects capable of being found using, for example, a defect review tool such as an SEM.

The deskew transform can be applied to the review image, such as using a controller. The controller can then validate that the image of the wafer from the review tool and the design file are or remain aligned.

If automatic pattern match fails, a user can manually mark deskew site for manual calculation of an offset. It can be determined that the deskew transform did not align the inspection image to the image from the review tool. At least one deskew site is manually marked. An offset between the inspection image to the image from the review tool is then calculated.

The deskew transform of FIG. 11 can be performed automatically.

For the embodiments of FIGS. 10 and 11, the deskew transform's success can be evaluated. For example, there can be score defined for the deskew transform representing the convergence of deskew transform with each alignment site offset used for the deskew calculation.

In either the embodiment of FIG. 10 or FIG. 11, a wafer may be aligned after it is loaded into the review tool. For example, the wafer may be aligned on a stage.

A review process may occur after the deskew transform of FIG. 10 or FIG. 11 is generated. Defects or other sites of interest may be reviewed using the review tool after the deskew transform.

In an instance, the automatic deskew process of FIG. 10 or FIG. 11, which may not use defect sites, can be used to calculate a complete affine transform. The affine transform can be a deskew transform between the inspection and review coordinate systems.

Prior to running the embodiments of FIGS. 10 and 11, the review tool may be set up. This can involve loading an inspection source and wafer, an alignment setup, die corner marking, test parameter setup, and/or saving a recipe.

The embodiments disclosed in FIGS. 10 and 11 can be performed independent of defects. Any unique alignment site can be used for deskew. Dependence on defects prevents automation of the deskew process and makes deskew impractical on high SNV rate inspections. Furthermore, reliance on defects can lead to failures. Correlation of design clips or inspection images and corresponding review images (e.g., SEM images) does not suffer from the same limitations because the design file contains the patterns which are printed on the wafer. Unique alignment sites or reference structures are used for deskew, which enables automatic correlation and/or calculation of a deskew transform. The embodiments disclosed in FIGS. 10 and 11 also are faster than manual deskew and less prone to human error.

Scaling may be performed on one or both corresponding images to substantially match the resolutions.

The embodiment described herein can remove any manual deskew or offset correction step from setup flow. An automatic deskew step may be executed before the review job in run mode. Depending on the availability of design clips at the unique alignment sites or reference structures chosen for deskew, the method for deskew can be chosen automatically. Thus, the embodiment of FIG. 10 or the embodiment of FIG. 11 can be selected depending on the availability of the design clips.

Each of the steps of the method may be performed as described further herein. The methods may also include any other step(s) that can be performed by the image acquisition subsystem and/or computer subsystem(s) or system(s) described herein. The steps are performed by one or more computer systems, which may be configured according to any of the embodiments described herein. In addition, the methods described above may be performed by any of the system embodiments described herein.

The embodiments disclosed herein may be configured for deskew of images from other specimens, such as reticles. For example, the embodiments described herein may be configured for the purposes of mask inspection, wafer inspection, or wafer metrology. In particular, the embodiments described herein may be installed on a computer node or computer cluster that is a component of or coupled to an output acquisition subsystem such as a broadband plasma inspection tool, an electron beam inspection tool or defect review tool, a mask inspection tool, a virtual inspection tool, etc. In this manner, the embodiments described herein may generate output that can be used for a variety of applications that include, but are not limited to, wafer inspection, mask inspection, electron beam inspection and review, metrology, etc. The controller can be modified as described above based on the specimen for which it will generate actual output.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
a review tool, wherein the review tool includes:
 a stage configured to hold a wafer; and
 an image generation system configured to generate an image of the wafer;
an electronic data storage unit in which one or more reference files are stored, each reference file having one or more alignment sites; and
a controller in electronic communication with the review tool, wherein the controller is configured to:
 receive the image of the wafer from the review tool;
 identify one or more alignment sites in the image of the wafer;
 receive a reference file from the electronic data storage unit corresponding to the image of the wafer from the review tool;
 mark at least one die corner on the wafer;
 compare one or more alignment sites in the reference file to one or more alignment sites in the image from the review tool;
 generate a deskew transform corresponding to the image of the wafer based on the one or more alignment sites;
 apply the deskew transform to the image of the wafer; and
 validate that the image of the wafer from the review tool and the reference file remain aligned after the deskew transform is applied by evaluating a convergence of the deskew transform with an alignment site offset used to calculate the deskew transform.

2. The system of claim 1, wherein the controller includes a processor and a communication port in electronic communication with the processor and the electronic data storage unit.

3. The system of claim 1, wherein the review tool is a scanning electron microscope.

4. The system of claim 1, wherein the image generation system is configured to use at least one of an electron beam, a broad band plasma, or a laser to generate the image of the wafer.

5. The system of claim 1, wherein the reference file is a design file.

6. The system of claim 1, wherein the reference file is an inspection image of the wafer.

7. The system of claim 1, wherein the image of the wafer does not contain a defect having a size from 3 μm to 50 μm.

8. The system of claim 1, wherein the deskew transform addresses scaling, rotation, non-orthogonality, and translation.

9. The system of claim 1, wherein the deskew transform is only based on devices or features with defects having a size less than 3 μm or greater than 50 μm.

10. A method comprising:
loading a wafer on a stage of a review tool;
receiving, from the review tool, an image of the wafer having one or more alignment sites;
receiving, at a controller, a design file corresponding to the wafer, the design file having one or more alignment sites;
marking at least one die corner on the wafer;
comparing, using the controller, the one or more alignment sites of the design file to the one or more alignment sites of the image from the review tool;
generating, using the controller, a deskew transform corresponding to the image of the wafer based on the one or more alignment sites;
applying the deskew transform to the image of the wafer using the controller; and
validating, using the controller, that the image of the wafer from the review tool and the design file remain aligned after the deskew transform is applied by evaluating a convergence of the deskew transform with an alignment site offset used to calculate the deskew transform.

11. The method of claim 10, wherein the image of the wafer from the review tool is a scanning electron microscope image.

12. The method of claim 10, wherein the image of the wafer does not contain a defect having a size from 3 μm to 50 μm.

13. The method of claim 10, wherein the deskew transform addresses scaling, rotation, non-orthogonality, and translation.

14. The method of claim 10, wherein the deskew transform is only based on devices or features with defects having a size less than 3 μm or greater than 50 μm.

15. A method comprising:
loading a wafer on a stage of a review tool;
receiving, from the review tool, an image of the wafer;
receiving, at a controller, an inspection image corresponding to the wafer;
marking at least one die corner on the wafer;
comparing, using the controller, alignment sites of the inspection image to alignment sites of the image from the review tool;
generating, using the controller, a deskew transform corresponding to the image of the wafer based on the one or more alignment sites;
applying the deskew transform to the image of the wafer using the controller; and
validating, using the controller, that the image of the wafer from the review tool and the inspection image remain aligned after the deskew transform is applied by evaluating a convergence of the deskew transform with an alignment site offset used to calculate the deskew transform.

16. The method of claim 15, further comprising:
manually marking at least one deskew site on the image of the wafer from the review tool; and
calculating an offset between the inspection image and the image from the review tool based on the marked deskew site.

17. The method of claim 15, wherein the image of the wafer from the review tool is a scanning electron microscope image.

18. The method of claim 15, wherein the image of the wafer does not contain a defect having a size from 3 µm to 50 µm.

19. The method of claim 15, wherein the deskew transform addresses scaling, rotation, non-orthogonality, and translation.

20. The method of claim 15, wherein the deskew transform is only based on devices or features with defects having a size less than 3 µm or greater than 50 µm.

* * * * *